(12) United States Patent
Müller et al.

(10) Patent No.: US 8,160,204 B2
(45) Date of Patent: Apr. 17, 2012

(54) METHOD AND DEVICE FOR IMRT VERIFICATION

(75) Inventors: Lutz Müller, Nürnberg (DE); Caterina Brusasco, Bossiere (BE); Björn Hårdemark, Stockholm (SE); Johan Löf, Djursholm (SE); Anders Murman, Uppsala (SE)

(73) Assignees: Ion Beam Applications S.A., Louvain-la-Neuve (BE); Raysearch Laboratories AB, Stockholm (SE)

( * ) Notice: Subject to any disclaimer, the term of this patent is extended or adjusted under 35 U.S.C. 154(b) by 210 days.

(21) Appl. No.: 12/513,139

(22) PCT Filed: Oct. 31, 2007

(86) PCT No.: PCT/EP2007/061787
§ 371 (c)(1),
(2), (4) Date: Mar. 18, 2010

(87) PCT Pub. No.: WO2008/053026
PCT Pub. Date: May 8, 2008

(65) Prior Publication Data
US 2010/0215147 A1      Aug. 26, 2010

(30) Foreign Application Priority Data
Nov. 3, 2006 (EP) .................................. 06123486

(51) Int. Cl.
*A61N 5/10* (2006.01)

(52) U.S. Cl. ........................................................ 378/65

(58) Field of Classification Search .................... 378/65
See application file for complete search history.

(56) References Cited

U.S. PATENT DOCUMENTS

| | | | |
|---|---|---|---|
| 5,394,452 A | 2/1995 | Swerdloff et al. |
| 6,038,284 A | 3/2000 | Hernandez-Guerra et al. |
| 6,853,702 B2 | 2/2005 | Renner |
| 2003/0174808 A1 | 9/2003 | Hughes et al. |

FOREIGN PATENT DOCUMENTS

WO        2003/092813 A1        11/2003

OTHER PUBLICATIONS

J.M. Kapatoes et al., "Delivery Verification in Sequential and Helical Tomotherapy." Physics in Medical and Biology, (1999) vol. 44, pp. 1815-1841.
J.M. Kapatoes et al., "A Feasible Method for Clinical Delivery Verification and Dose Reconstruction in Tomotherapy." Medical Physics, Apr. 2001, vol. 28, Issue 4, pp. 528-542.
J.M. Kapatoes et al., "On the Accuracy and Effectiveness of Dose Reconstruction for Tomotherapy." Physics in Medical and Biology, (2001) vol. 46, pp. 943-966.
International Search Report, International Application No. PCT/EP2007/061787; date of completion Feb. 19, 2008, 4 pages.
International Search Report, International Application No. PCT/EP2007/061836; date of completion Mar. 20, 2008, 4 pages.

*Primary Examiner* — Courtney Thomas
(74) *Attorney, Agent, or Firm* — Fitch, Even, Tabin & Flannery, LLP (57) ABSTRACT

The present invention relates to a method and device for verification of the quality of a radiation beam in conformal radiation therapy, and in particular for IMRT (Intensity Modulated Radiation Therapy) applications.

16 Claims, 6 Drawing Sheets

METHOD AND DEVICE FOR IMRT VERIFICATION

CROSS REFERENCE TO RELATED APPLICATIONS

This application is a national phase application of International Application No. PCT/EP2007/061787, filed Oct. 31, 2007, claiming priority to European Patent Application No. 06123486.0, filed Nov. 3, 2006, which are incorporated by reference herein in their entirety.

FIELD OF THE INVENTION

The present invention relates generally to intensity modulated radiation therapy (IMRT) used to deliver radiation doses. More particularly, the present invention relates to a method and device for computing a 3D dose distribution to be compared to a correspondent treatment plan, as well as for allowing quality assurance (QA) in IMRT. The present invention also relates to a method and device for correcting errors detected during said QA.

STATE OF THE ART

IMRT is a type of conformal radiation, which shapes radiation doses to closely match the shape of a target area. More particularly, IMRT is an advanced high-precision radiotherapy that utilizes computer-controlled x-ray or electron beams in order to deliver precise radiation doses to a malignant tumour or specific areas within the tumour. By the way, it can also be used to cure non malignant tumour. The radiation dose is designed to conform to the three-dimensional (3-D) shape of the tumour by modulating or controlling the intensity of the radiation beam in such a way as to focus, as much as possible, the higher radiation dose to the tumour while minimizing radiation exposure to healthy surrounding tissues. IMRT usually uses a multi leaf collimator (MLC) that can vary the radiation beam intensity of each field composing the patient treatment across the target. Therefore, the healthy surrounding tissue receives a much smaller dose of radiation than the tumour does. In addition and for special cases, there can even be a dosage that varies within the tumour. Treatment is carefully planned by using 3-D computed tomography (CT) images of the patient. Such images are used in conjunction with computerized dose calculations in order to find out the beam cross section intensity pattern that will best conform to the dose to the tumour shape. Typically, combinations of several intensity-modulated fields coming from different beam directions produce a custom tailored radiation dose that maximizes tumour dose while also protecting adjacent normal tissues. With the IMRT approach, higher and more efficient radiation doses can safely be delivered to tumours with fewer side effects compared to conventional radiotherapy techniques. Even if doses are not increased, IMRT has the potential to reduce treatment toxicity.

Treatment planning for IMRT is obviously more complex than for conventional radiation therapy, extending treatment planning time required for each patient. Unlike the conventional delivery, the complexity of the IMRT treatments makes it difficult for the operators to detect during the delivery possible deviations from the planned sequence of irradiations.

Before planning a treatment, a physical examination and medical history review is performed. This comprises CT scanning from which the radiation oncologist specifies the three-dimensional shape of the tumour and normal tissues. The dosimetrist and medical radiation physicist use this information to define the treatment plan. Several additional scanning procedures, including positron emission tomography (PET) and magnetic resonance imaging (MRI), might also be required for IMRT planning. These diagnostic images help the radiation oncologist to determine the precise location of the tumour target. Typically, IMRT sessions begin about a week after simulation. Typically, patients are scheduled for IMRT sessions five days a week for six to ten weeks.

The efficacy of radiation therapy relies on the accuracy of dose delivery, and, as a result, quality assurance procedures used to detect dosimetric errors are of critical importance. Examples of such procedures include measurements in order to verify the accuracy of the delivery of the planned doses calculated by treatment planning systems, and the acquisition of orthogonal portal images to ensure accurate patient positioning with respect to the treatment machine isocenter.

IMRT places even more stringent demands on these verification procedures, and makes them even more essential. The high dose gradients in IMRT fields make single point-dose measurements inadequate in verifying the significantly non uniform dose distributions. Errors in the Individual IMRT beam dose distributions calculated by treatment planning systems can occur because interleaf leakage of the multi-leaf collimator (MLC) is, for example, not accurately accounted for. The potential for systematic errors in the transfer of MLC leaf sequence files from the treatment planning computer to the record and verify system, and in the mechanical accuracy of the MLC leaf movements during beam delivery further necessitates the use of accurate IMRT verification strategies.

Figure 1:
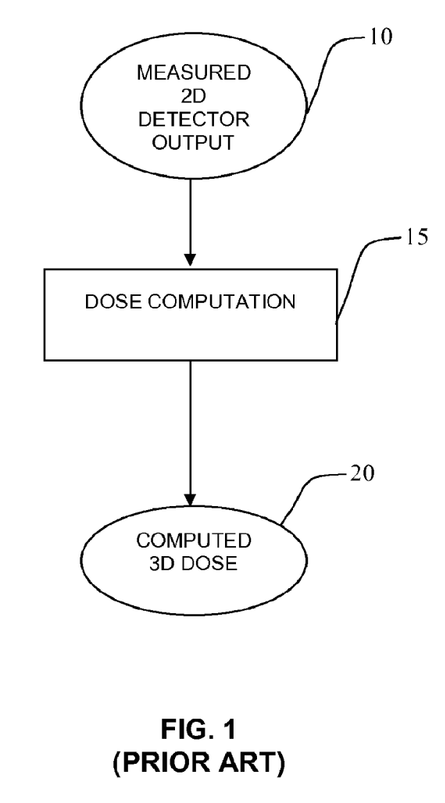
FIG. 1 represents a method for 3D dose computation according to the prior art.

U.S. Pat. No. 6,853,702, discloses a method for treatment verification in radiation therapy. In this method, one measures the output of treatment beams over the area of the beam in a plane perpendicular to the central ray of the beam. This is accomplished by using a detector in front of the patient and one uses said measured output to calculate the dose to the patient using a dose algorithm. By referring to FIG. 1, the measured 2D detector output 10 (which corresponds to the captured images 40 of the document U.S. Pat. No. 6,853,702), is directly used to obtain the computed 3D dose 20 (corresponding to the dose distribution 58 of said document) by means of a dose algorithm and a computer program, which performs a dose computation 15. However, this method relies on the assumption that the measured field images represent the photon fluence distribution at isocenter of each field. At least two main characteristics distinguish the 2D detector output, that are measured close to the accelerator head, from the 2D fluence distribution delivered at isocenter: on the one hand, the presence of electron contamination in the measurements and on the other hand the distortion in the 2D distributions due to the finite source size and the shorter source to detector distance. As a consequence, this method requires significant build-up bolus materials to shield out electron contamination from the imaging device. Furthermore, this method does not provide any solution to the problem of the distortion into the images that are captured close to the accelerator head with respect to those that are captured at isocenter, where the dose distribution 58 has to be computed.

It is also known from document WO 03/092813 a method for calibrating detectors to be used during treatment of a patient. This method is intended for verifying the accuracy of the delivery of a radiation treatment beam generated by a radiation apparatus to a patient. By referring to FIG. 1', this method mainly comprises two irradiation steps. During the first step, a first irradiation to a phantom (step A) is delivered and, at each time-interval, measurements (100) of the delivered dose in a phantom and information regarding the irradiation collected (200) by information means located between the source of said radiation beam and said phantom (by using for example an imaging system such as a film or EPID) are put in relationship (step B). By using this relationship it is possible to calculate calibration factors (300). According with this document, said information means may be either measurements by means of a detector or positions of Multi Leaf Collimator leaves. During a second irradiation step (step C), a patient is irradiated and once again information regarding the irradiation (400) is collected again by information means located between the source of said radiation beam and said phantom. This collected information (400) is then analysed together (D) with previous calibration factors (300) in order to obtain the total dose to the patient (500). This method therefore requires two subsequent irradiations, the first one when irradiating a phantom and a second one when irradiating a patient. It is evident that such a method is time-consuming and not accurate. Furthermore, this method never addresses to the verification of the radiation apparatus before the actual treatment of a patient.

Accordingly, no practical solution is proposed to provide an accurate radiation apparatus and dose verification method as well as to perform an easy and fast dose computation that overcomes the drawbacks above mentioned.

AIMS OF THE INVENTION

The present invention aims to provide a IMRT verification device and method that do not present the drawbacks of the state of the art.

In particular, the present invention aims to reduce the extended, time consuming machine QA and patient plan verification needed for IMRT.

Furthermore, the present invention aims to considerably enhance the state of the art method of patient specific IMRT verification, by allowing 3D dose verification in the patient's anatomical structures.

SUMMARY OF THE INVENTION

According with a first aspect of the present invention a method for radiation therapy apparatus verification is described. It comprises the steps of:
providing a radiation therapy apparatus for delivery of a radiation beam, said radiation therapy apparatus being configurable for a given radiation treatment;
providing a description or image of a target, said description or image comprising the 3D shape, density distribution and position of said target;
providing an electronic detector device capable of providing measured 2D detector responses of said radiation beam in a plane perpendicular to said radiation beam;
providing a beam model of said radiation therapy apparatus, said beam model being based on a set of machine parameters and on a set of beam model parameters;
providing values for said set of machine parameters and for said set of beam model parameters defining a set configuration;
irradiating with said radiation therapy apparatus having said set of machine parameters, and providing measured 2D detector responses caused by said radiation beam for each set configuration;
reconstructing the delivered photon fluence distributions corresponding to the radiation beam, based on the measured 2D detector responses, on a fluence algorithm, on said set of machine parameters, on said set of beam model parameters and on said beam model;
computing the 3D delivered dose distributions based on said reconstructed delivered fluence distributions, on a dose algorithm and on said description or image of the target.

Advantageously, the method according to the first aspect of the present invention further comprises the steps of: providing a detector model; computing 2D detector responses based on said reconstructed delivered photon fluence, on said detector model, and on a response calculation algorithm; comparing said computed 2D detector responses to said measured detector responses; providing new values to said set of machine parameters and reconstructing the delivered photon fluence by incorporating possible errors in said reconstruction; repeating these four steps until the value difference between said computed 2D detector responses and the measured 2D detector response minimize a scoring function.

According to a preferred embodiment of the first aspect of the present invention, said step of providing a set of machine parameters for said radiation therapy apparatus, is importing a treatment plan from a Treatment Planning System.

More advantageously, according to this preferred embodiment of the first aspect of the present invention, the method further comprises the steps of: importing computed or predicted 3D dose distributions in said description or image of the target, corresponding to said imported TP; comparing delivered 3D dose distributions with the computed or predicted 3D dose distributions; reporting a set of parameters resulting from said comparison.

Advantageously, according to another preferred embodiment of the first aspect of the invention, said step of providing a set of machine parameters for said radiation therapy apparatus is providing a set of user defined specifications. More advantageously, it further comprises the steps of: extracting subsets of the 3D delivered dose distributions in said description or image of the target; reporting a set of parameters of said subsets for assessing the quality of the delivery of the RT apparatus. Accordingly, the method further comprises the step of identifying possible causes of errors due to possible mismatches of said 3D delivered dose distributions with said predicted or computed 3D dose distributions in said description or image of the target or in case of unexpected parameter values in said reported set of parameters.

Advantageously, according to the first aspect of the invention, the method further comprises the step of suggesting modifications to the TP.

According to a second aspect of the present invention a device for radiation therapy apparatus verification is described. This device comprises irradiation means, electronic 2D detectors; a main software; a dose calculation module software which are arranged in such a way to perform the method according to the first aspect of the present invention.

BRIEF DESCRIPTION OF THE DRAWINGS

FIG. 1' represents another method for 3D dose computation according to the prior art.

DETAILED DESCRIPTION OF PREFERRED EMBODIMENTS OF THE PRESENT INVENTION

The present invention is intended to be used with a radiation therapy apparatus, which delivers high energy x-ray from an isocentric gantry linear accelerator, and especially with an IMRT apparatus wherein the beam modulation is accomplished by means of a multi leaf collimator (MLC) or by jaws.

A beam model is a mathematical description of a radiation therapy apparatus in general, which contains a number of parameters. These parameters take into account e.g. the characteristics of the accelerator (energy spectrum, lateral beam quality variations), the shapes and positions of the effective radiation sources, and the geometry and material of the beam shaping devices. A fluence computation algorithm is a set of mathematical rules which compute the fluence according to the beam model and a given parameter set. The representation of the computed fluence (units, coordinate systems) is such that it is compatible with additional computational procedures for computing deposited dose in tissue and/or detector response. Useful descriptions of basic beam modelling techniques are provided, for example, by Wolfgang A. Tomé, "Beam Modelling for a Convolution/Superposition-Based Treatment Planning System", Medical Dosimetry, Vol. 27, No. 1, pp. 11-19, 2002; or by Nikos Papanikolaou, "Investigation of the convolution method for polyenergetic spectra", Med. Phys. 20(5), 1993.

Depth dose curves and beam profiles for various depths are measured for establishing the parameters of the beam that the treatment machine can deliver. The beam model parameters are then optimised in order to give the best match between model predictions and measured dosimetric data. This beam model is then used in IMRT Treatment Planning Systems to calculate the 3-dimensional dose distribution resulting from field modulation patterns. Various strategies are used in TPSs to optimise the machine settings (numbers of fields, dose per field, field modulation, gantry angles, etc. . . . ) in order to reach as close as possible the therapeutic aims.

According to a preferred embodiment, the present invention relates to a method for radiation therapy apparatus verification characterized in that it comprises the steps of:

providing a radiation therapy apparatus for delivery of a radiation beam, said radiation therapy apparatus being configurable for a given radiation treatment;

providing a description of a target (330), said description comprising the 3D shape, density distribution and position of said target;

providing an electronic detector system capable of providing 2D responses (310) of said radiation beam in a plane perpendicular to the treatment beam;

providing a beam model (210) of said radiation therapy apparatus, said beam model (210) being based on a set of machine parameters (250) and on a set of beam model parameters (240);

providing values for said set of machine parameters (250) and for said set of beam model parameters (240);

irradiating said target with said radiation therapy apparatus having said set of machine parameters (250), and providing measured detector responses (310) caused by radiation beams for each configuration of this set;

reconstructing the delivered photon fluence distributions (320, 5311) corresponding to the irradiated radiation beams, based on the measured detector responses (310), on a fluence algorithm (300), on said set of machine parameters (250), on said set of beam model parameters (240) and on said beam model (210);

computing the 3D delivered dose distributions (350, 5341) in said target based on said reconstructed delivered fluence distributions (320), on a dose algorithm (340) and on said description of the target (330).

Preferably, it further comprises the steps of:

a. providing a detector model (400);

b. computing 2D detector responses (420, S411) based on said reconstructed delivered photon fluence (320), on said detector model (400), and on a response calculation algorithm (410);

c. comparing said 2D computed detector responses (420, 5430) to said measured detector responses (310);

d. providing new values for said set of machine parameters (250) and reconstructing the delivered photon fluence (320, 450) by incorporating possible errors (S431) in said reconstruction;

e. repeating steps a to d until the value difference between said computed 2D detector responses (420) and the measured 2D detector response (310) minimizes a scoring function.

Preferably, said step of providing a set of machine parameters (250) for said radiation therapy apparatus is importing a treatment plan from a Treatment Planning System.

Preferably, it further comprises the steps of:

importing predicted 3-D dose distributions in the target, corresponding to said imported treatment plan;

comparing said 3-D delivered dose distributions with the predicted 3-D dose distributions (350);

reporting a set of parameters resulting from said comparison.

Preferably, said step of providing a set of machine parameters (250) for said radiation therapy apparatus is providing a set of user defined specifications.

Preferably, it further comprises the steps of:

extracting subsets of the 3-D delivered dose distributions in the target;

providing a report of parameters of said subsets for assessing the quality of the delivery of the radiation therapy apparatus.

Preferably, it further comprises the step of identifying possible causes of errors due to possible mismatches of said 3-D delivered dose distributions with said predicted 3-D dose distributions (350) in the target or in case of unexpected parameter values in said report of parameters.

Preferably, it further comprises the step of suggesting modifications to the treatment plan.

According to a preferred embodiment, the present invention also relates to a device for radiation therapy apparatus verification, comprising:

electronic 2-D detectors;

a main software;

a dose calculation module software;

characterized in that said electronic 2-D detectors, said main software and said dose calculation module software are arranged to perform the method hereabove.

In a preferred embodiment of the invention, a 2-dimensional transmission detector is required to provide a 2-dimensional map of measurements on a plane orthogonal to the beam direction. A technology used to realize such a detector for hadron beams is described by Bonin and al. in "A pixel chamber to monitor the beam performances in hadron therapy", Nuclear Instruments and Methods in Physics research, A 519 (2004)-674-686. This document describes a device made up of a 2-D array of 1024 ionisation chambers arranged in a regular matrix of 32×32 pixels. This technology is also used in the commercial product MatriXX manufactured by the Applicant, which has been modified for usage with photon beams by providing lateral electronic equilibrium for each chamber of the detector.

Figure 2:
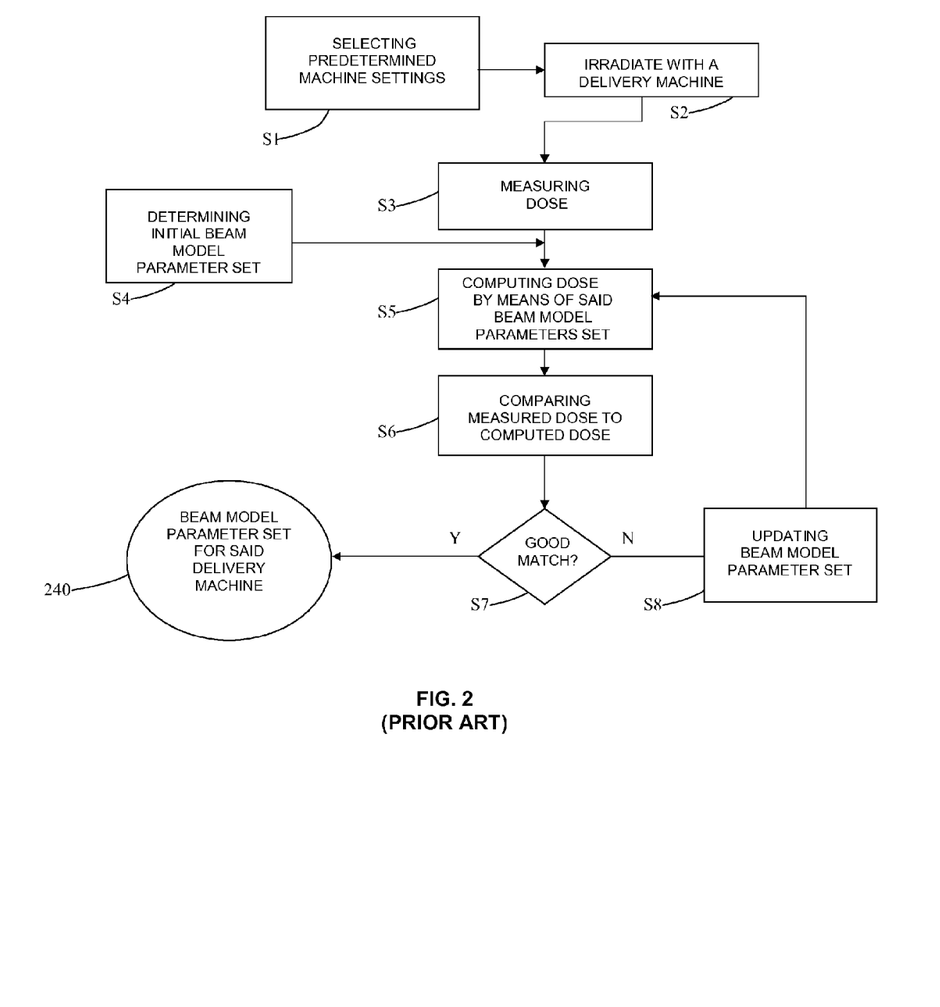
FIG. 2 is a dataflow diagram which represents the state of the art method to adapt a beam model to a given delivery machine by finding a beam model parameters set that best fits the given delivery machine.

FIG. 2 is a dataflow diagram which represents the state of the art method to adapt a beam model to a given delivery machine by finding a beam model parameters set that best fits the given delivery machine. As shown in step S1, the operator selects some predetermined machine settings. Next, as shown now in step S2 and S3, the delivery machine to be modelled is used to irradiate a phantom using said predetermined machine settings, and, by using detector means, the dose is measured. In step S4, a beam model parameters set, for a similar delivery machine, is selected and using said beam model parameters set the dose is computed in the same points as the measurements. The computed and measured doses are then compared in step S5. Should the user find the match adequate, in test S7, the current beam model parameter set 240 is said to represent the delivery machine. Otherwise, the beam model parameters set is modified, manually or automatically, as shown in step S8 and a dose computation is carried out, returning to step S5.

Figure 3:
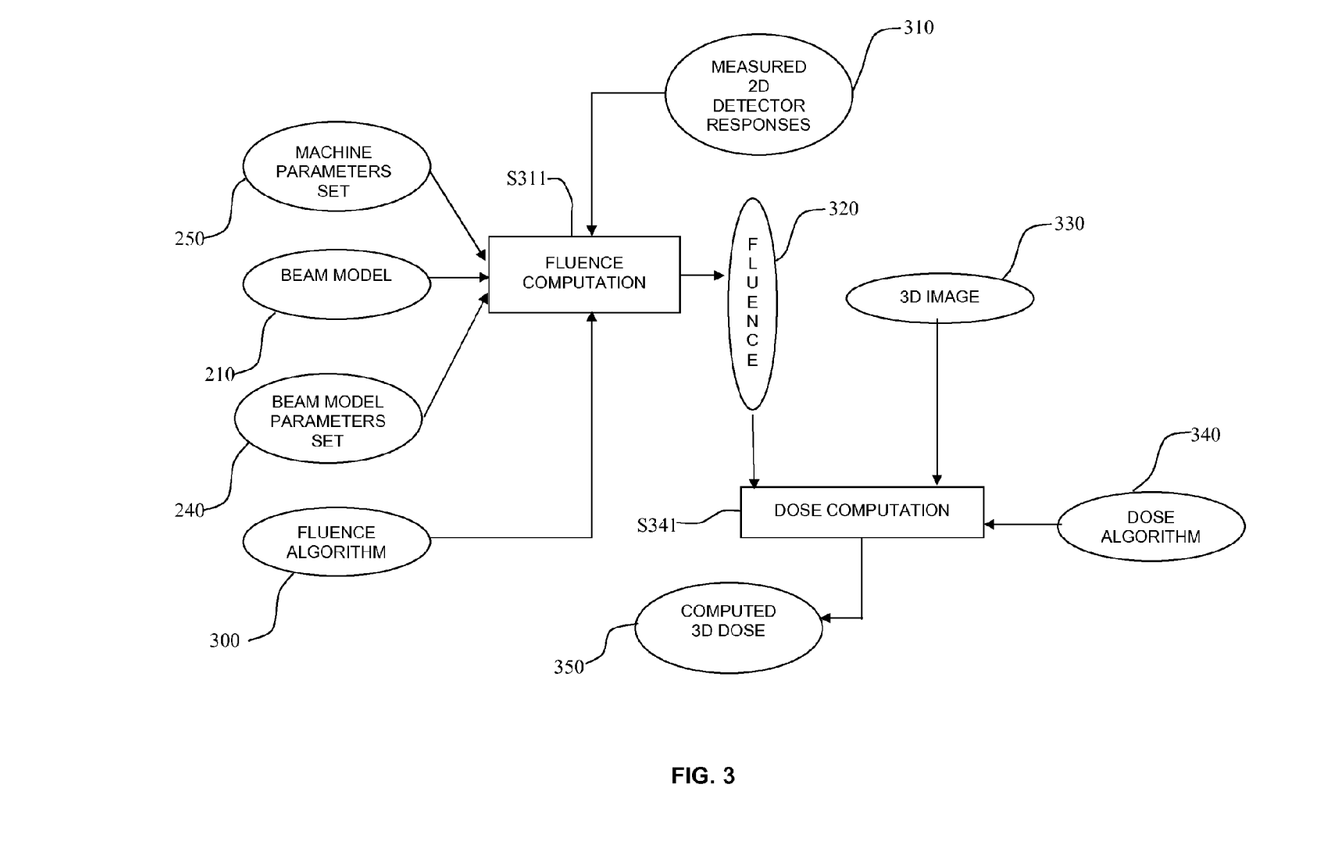
FIG. 3 is a dataflow diagram which represents a method according to the invention.

FIG. 3 is a dataflow diagram which represents a method according to the invention. Based on said beam model parameters set 240, on machine settings 250 (which are chosen according to the machine commissioning and to the settings of the treatment machine for the given treatment (energy and dose, dose-rate, MLC position, on the beam model 210 of the RT apparatus, on a fluence algorithm 300 and on the measured 2D detector responses 310, one obtains, as shown in step S311, the corresponding fluence 320. An example of such a fluence algorithm is described in Yong Yang, "A three-source model for the calculation of head scatter factors", Med. Phys. 29(9), 2002.

The corresponding fluence 320 is then used together with a 3D image 330, representing a description of the target geometry and density, and a dose algorithm 340, in order to obtain the computed 3D dose 350 in the target, as shown in step S341. Such a dose algorithm is, for example, the one described by Anders Ahnesjö, "Collapsed Cone Convolution of Radiant Energy for Photon Calculation in Heterogeneous Media", Med. Phys. 16(4), 1989.

It should be noticed that by using said workflow for calculating the 3-dimensional dose distribution in said description of the target, the irradiation of a real phantom is no more required for providing a measured dose distribution in the phantom, in contrast with prior art (such as the document WO 03/092813 for example). Therefore, the irradiation step of the method is performed only once without any phantom or patient located in the direction of the beam.

Figure 4:
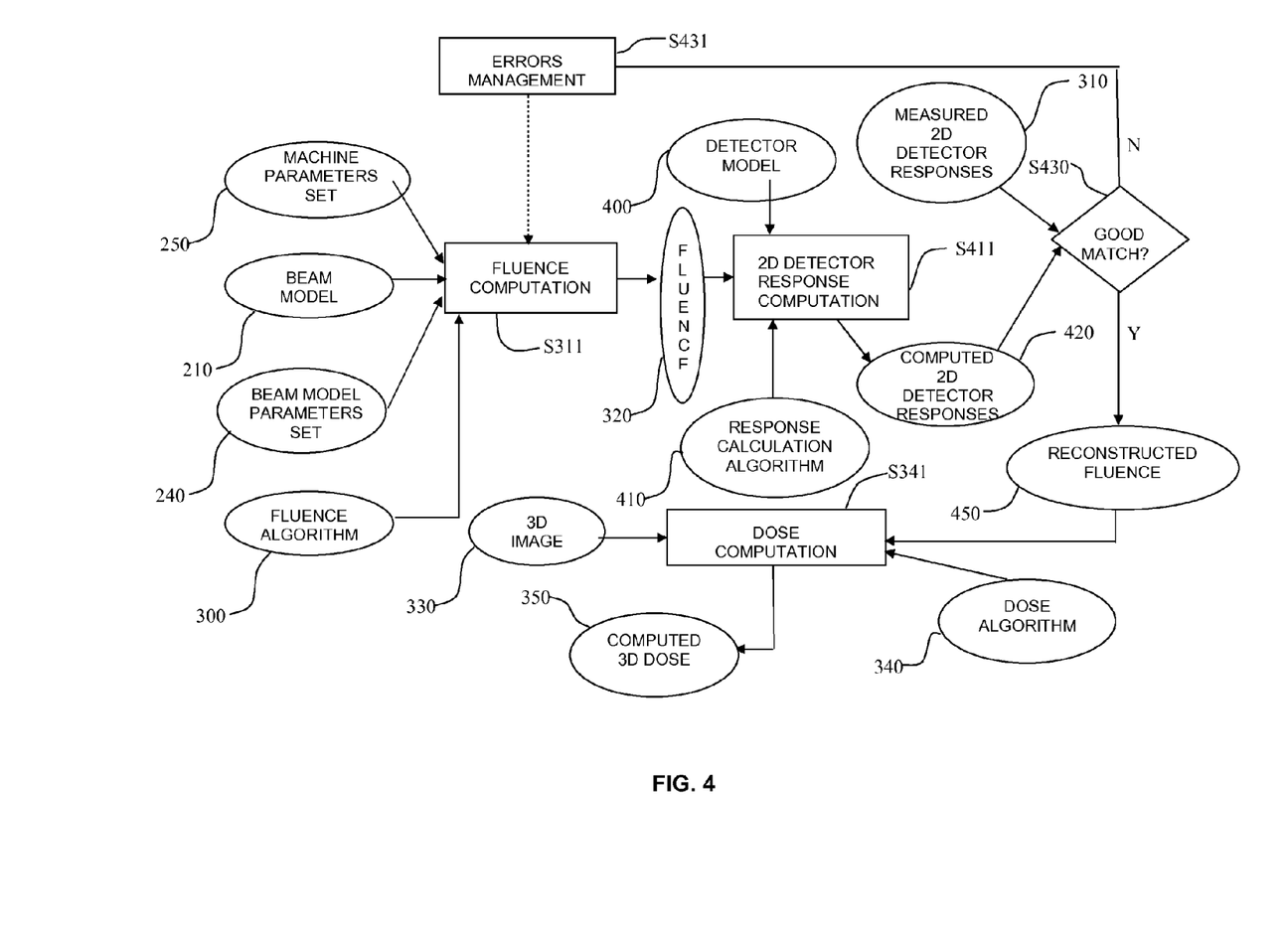
FIG. 4 is a dataflow diagram which represents another method according to the invention.

We refer now to FIG. 4. According to the invention, an optimization cycle is performed in order to provide a satisfactory computation of the fluence directed to a target. Once the corresponding fluence 320 is established as above-described, based on it one calculates the corresponding 2D detector response 420, as shown in step S411. This response calculation is based on Monte Carlo simulations of incident particles on the detector means surface, wherein all added buildup materials are also taken into account. This calculation is facilitated by a detector model 400 which describes the geometry of the device, and a response calculation algorithm 410 which describes the device response to the irradiation. The computed 2D detector response 420 is then compared to the measured 2D detector response 310 by a scoring function S430 quantifying the difference between them. In order to minimize this scoring function S430 (and thus the difference), it is possible to incorporate some delivery and/or modelling errors directly into the fluence computation (for example, by adjusting effective leaf positions, effective transmission, effective tongue-and-groove effects, effective output and effective source positions), as shown in step S431. Should this iterative modification of the fluence converge to a sufficiently small difference in the scoring function 5430, it is considered that the last modified fluence 320 faithfully represents the fluence directed to the target, which is denoted as the reconstructed fluence 450. Once again, the reconstructed fluence 450 is used together with a 3D image 330 representing a description of the target geometry and density and a dose algorithm 340 in order to obtain the computed 3D dose 350 in the target.

The iterative method could also not converge, in which case there is no reconstructed fluence, but rather an indication of failure. This would typically occur if the measured response is very different from the expected one, i.e. if the wrong plan is delivered, if a segment is omitted, if significant MLC failures occur etc.

A 3D dose distribution constitutes a large data set, typically in the order of a million or more data points. Comparing two such distributions therefore requires some tools. One set of such tools comprises different types of dose volume statistics, typically based on predefined volumes (regions) of interest. The most common dose volume tool is the dose volume histogram (DVH). Another set of tools are based on extracting 2D subsets from the 3D data. The 2D subsets typically constitute planes normal to the major axes. On such planes, the dose can be represented by color tables, isodose lines or as a 3D surface. Lines can be defined on the planes, and the dose extracted along these lines, and displayed in 2D graphs. Furthermore, point-by-point information such as the dose value and the coordinates can be obtained by selecting a point either on a plane or on a line.

When the target is an homogeneous water phantom, the comparison between the 3D delivered dose distributions with the predicted 3D dose distributions permits on the one hand to extract a report of parameters for assessing the quality of the delivery of the RT apparatus (defining a set of parameters: flatness, symmetry, penumbra, field shaping, leaves position, . . . ), and on the other hand to identify possible causes of errors due to mismatches in said comparison or errors due to unexpected parameter values in said report of parameters.

Whatever is the target, however, a set of different alterations, depending on errors, can be evaluated and executed for modifying the RT apparatus configuration, i.e. the machine settings. Possible actions comprise: adjusting segment weights to compensate for output modelling errors; adjusting MLC/jaw positions to compensate for leaf tip transmission modelling errors and/or systematic positioning errors; etc.

Figure 5:
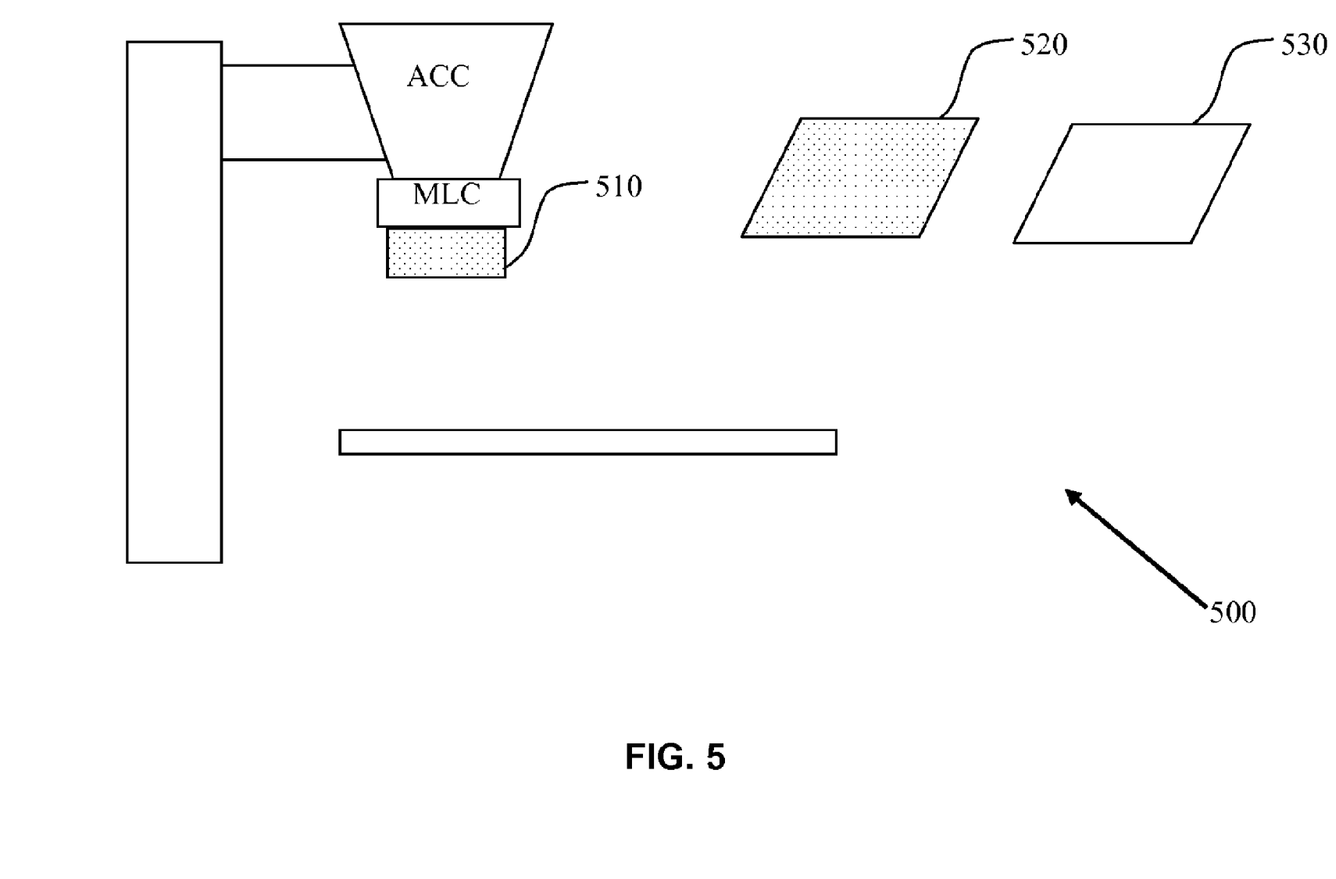
FIG. 5 is a device for radiation therapy verification according to the invention.

FIG. 5 is a device for radiation therapy verification according to the invention. The device 500 comprises a an electronic detector 510 capable of providing 2d responses 310 of said radiation beam emitted by a radiation source ACC and collimated through a collimator MLC. The device 500 further comprises processing means 520a and a dose calculation module software 530 capable of performing the method above described and providing the verification of the radiation apparatus.

Accordingly, many advantages are reached by using the present invention. In fact the embodiments of the invention allow to:

quickly identify possible sources of errors during QA and patient plan verification;

perform a 3D dose verification in the patient's anatomy which is independent of original TPS, by using patient's anatomy data and a dose algorithm independent from the TPS;

provide the oncologist with data analysis tools in order to perform studies of protocols for given tumour entities and to compare results from different TPSs and radiation sources;

provide easy calibration procedures for MLC.

verify the delivered dose distribution directly on the patient anatomy and not only in homogeneous phantoms.

reduce global costs due to the cumbersome and long lasting state-of-art measurements and routine equipment QA tests.

The invention claimed is:

1. A method for radiation therapy apparatus verification comprising the steps of:

providing a radiation therapy apparatus for delivery of a radiation beam, said radiation therapy apparatus being configurable for a given radiation treatment;

providing a description or an image of a target, said description or image comprising a 3D shape, density distribution and position of said target;

providing an electronic detector device configured to provide measured 2D detector responses of said radiation beam in a plane perpendicular to said radiation beam;

providing a beam model of said radiation therapy apparatus, said beam model being based on a set of machine parameters and on a set of beam model parameters;

providing values for said set of machine parameters and for said set of beam model parameters defining a set configuration;

irradiating with said radiation therapy apparatus having said set of machine parameters, and providing measured 2D detector responses caused by said radiation beam for each set configuration;

reconstructing delivered photon fluence distributions corresponding to the radiation beam, based on the measured 2D detector responses, on a fluence algorithm, on said set of machine parameters, on said set of beam model parameters and on said beam model; and computing 3D delivered dose distributions based on said reconstructed delivered fluence distributions, on a dose algorithm and on said description or image of the target.

2. The method according to claim 1, the method further comprising:

a. providing a detector model;
 b. computing 2D detector responses based on said reconstructed delivered photon fluence, on said detector model, and on a response calculation algorithm;
 c. comparing said computed 2D detector responses to said measured 2D detector responses;
 d. providing new values for said set of machine parameters and reconstructing the delivered photon fluence by incorporating possible errors in said reconstruction; and
 e. repeating steps a to d until the value difference between said computed 2D detector responses and the measured 2D detector response minimizes a scoring function.

3. The method according to claim 2, wherein the step of providing a set of machine parameters for said radiation therapy apparatus comprises importing a treatment plan from a treatment planning system.

4. The method according to claim 3, the method further comprising the steps of:

importing computed or predicted 3D dose distributions in said description or image of the target, corresponding to said imported treatment plan;

comparing the 3D delivered dose distributions with the computed or predicted 3D dose distributions; and reporting a set of parameters resulting from said comparison.

5. The method according to claim 2, wherein said step of providing a set of machine parameters for said radiation therapy apparatus comprises providing a set of user defined specifications.

6. The method according to claim 5, the method further comprising the steps of:

extracting subsets of the 3D delivered dose distributions in said description or image of the target; and reporting a set of parameters of said subsets for assessing the quality of the delivery of the radiation therapy apparatus.

7. The method according to claim 6, the method further comprising: identifying possible causes of errors due to possible mismatches of said 3D delivered dose distributions with said predicted or computed 3D dose distributions in said description or image of the target or, in case of unexpected parameter values in said reported set of parameters.

8. The method according to claim 7, the method further comprising the step of suggesting modifications to the treatment plan.

9. A device for radiation therapy apparatus verification, said radiation therapy apparatus being configurable for a given radiation treatment, the device comprising:

an irradiation device;

an electronic 2-D detector device configured to provide measured 2D detector responses of said radiation beam in a plane perpendicular to said radiation beam;

a processor configured to carry out the steps of:

a. providing a description of a target, said description comprising a 3D shape, density distribution and a position of said target;
 b. providing a beam model of said radiation therapy apparatus, said beam model being based on a set of machine parameters and on a set of beam model parameters;
 c. providing values for said set of machine parameters and for said set of beam model parameters defining a set configuration; and
 d. reconstructing the delivered photon fluence distributions corresponding to the radiation beam, based on the measured 2D detector responses, on a fluence algorithm, on said set of machine parameters, on said set of beam model parameters and on said beam model; and a dose calculation module software configured to compute 3D delivered dose distributions in said description of the target based on said reconstructed delivered fluence distributions, on a dose algorithm and on said description of the target.

10. The device for radiation therapy apparatus verification according to claim 9, wherein the processor is configured to carry out the steps of:

f. providing a detector model for said electronic 2D detectors;
 g. computing 2D detector responses based on said reconstructed delivered photon fluence, on said detector model, and on a response calculation algorithm;
 h. comparing said computed 2D detector responses to said detector responses measured when irradiating with said radiation therapy apparatus having said set of machine parameters; and i. providing new values for said set of machine parameters and reconstructing the delivered photon fluence by incorporating possible errors in said reconstruction;

j. repeating steps f) to i) until the value a difference between said computed 2D detector responses and the measured 2D detector response minimizes a scoring function.

11. The device for radiation therapy apparatus verification according to claim 9, wherein the processor uses a treatment plan from a treatment planning system which provides a set of machine parameters for said radiation therapy apparatus.

12. The device for radiation therapy apparatus verification according to claim 11, wherein the processor is configured to perform the steps comprising:
   importing predicted 3-D dose distributions in said description of the target, corresponding to said imported treatment plan;
   comparing said 3-D delivered dose distributions with predicted 3-D dose distributions; and
   reporting a set of parameters resulting from said comparison.

13. The device for radiation therapy apparatus verification according to claim 9, wherein the processor provides a set of machine parameters (250) for said radiation therapy apparatus by providing a set of user defined specifications.

14. The device according to claim 13, wherein the processor is configured to perform the steps of:
   extracting subsets of the 3-D delivered dose distributions in said description of the target; and
   providing a report of parameters of said subsets for assessing the quality of the delivery of the radiation therapy apparatus.

15. The device according to claim 14, wherein the processor is configured to perform the step of identifying possible causes of errors due to possible mismatches of said 3-D delivered dose distributions with said predicted 3-D dose distributions (350) in said description of the target or in case of unexpected parameter values in said report of parameters.

16. The device according to claim 15, wherein the device is further configured to suggest modifications to the treatment plan.

* * * * *